United States Patent [19]
Plambeck et al.

[11] Patent Number: 5,281,111
[45] Date of Patent: Jan. 25, 1994

[54] CARTRIDGE FOR DRUG INFUSION PUMP

[75] Inventors: Gregg E. Plambeck, San Clemente; Thomas A. Kramer, San Carlos, both of Calif.

[73] Assignee: Abbott Laboratories, Abbott Park, Ill.

[21] Appl. No.: 996,326

[22] Filed: Dec. 23, 1992

[51] Int. Cl.$^5$ .................... F04B 43/08; F04B 43/12
[52] U.S. Cl. .................... 417/476; 604/153
[58] Field of Search .................... 47/474, 476, 477; 604/153

[56] References Cited

U.S. PATENT DOCUMENTS

| | | | |
|---|---|---|---|
| 4,559,040 | 12/1985 | Morres et al. | 417/476 |
| 5,057,081 | 10/1991 | Sunderland | 417/474 |
| 5,181,842 | 1/1993 | Sunderland | 417/474 |
| 5,213,483 | 5/1993 | Flamerty | 417/474 |

Primary Examiner—Edward K. Look
Assistant Examiner—Peter Korytnyk
Attorney, Agent, or Firm—Harry G. Thibault; Robert E. Wexler

[57] ABSTRACT

An improved segmented peristaltic cartridge comprising a housing and a cover for assembly in snap-fit relation, said housing and cover defining a pumping chamber having an open segment therein wherein the pumping chamber holds a rotor, a rotor sleeve and a section of flexible tubing looped around the rotor and connected to respective inlet and outlet ports of the cartridge. Mounted on an exterior face of the housing is a safety shield which protects the tubing exposed in the open segment of the cartridge when the cartridge is inserted into a motor pump frame. The cartridge includes free standing walls on the cartridge housing engaging registration surfaces on the cartridge cover, an improved dowel pin structure and peripheral ribs on the rear cover and engaging a rear face of the rotor to minimize friction therebetween.

6 Claims, 7 Drawing Sheets

CARTRIDGE FOR DRUG INFUSION PUMP

BACKGROUND OF THE INVENTION

U.S. Pat. No. 4,559,040 described an improvement to a miniature peristaltic pump in which a cartridge of the pump holds a rotor, a sleeve mounted on the rotor and a length of compressible tubing having opposite ends, wrapped around the sleeve. The cartridge is formed by two members, the "housing" and the "cover". The rotor is eccentrically formed to radially squeeze the resilient tubing. The tubing is in a single loop inside the circular pumping cartridge. The cyclic squeezing of the tubing by the rotor and the associated sleeve forces fluid from an inlet port to an outlet port of the pump.

Ideally, a disposable pump cartridge should be assembled and ready for insertion by connecting external inlet and outlet ports to tubing running from the source of medication to the patient. However, the structure of a closed continuous pump cartridge and the eccentricity of the rotor operate to pinch the resilient tube inside the chamber. Pinching of the tubing results in a permanent occlusion in the tubing. Further, pinching of the tubing also prevents gravity flushing of air bubbles from the system. If a chord segment is removed from the circumference of the pump cartridge for storage purposes, the resilient tubing is not pinched at a set position of the rotor high point during storage, and the tubing remains an open and resilient channel. The chord segment comprising a separate component associated with a motorized drive mechanism (motor frame) is combined with the cartridge immediately prior to use, to avoid an occlusion in the tubing during storage.

U.S. Pat. No. 4,559,040 describes such an improvement on a small peristaltic pump used in medical applications wherein a cartridge separate from the motor is preloaded with tubing and stored for future and rapid use. The cartridge described therein enables the tubing to be loaded with medicant by gravity flow while inserted in the head because the cap as not attached to the cartridge and the fluid passage through the cartridge is unoccluded.

The aforementioned U.S. patent describes a segmented cartridge for a peristaltic pump, wherein by removing a chord segment of the periphery of a pump chamber of the cartridge, an open area is created and the resilient tubing used by the peristaltic pump is not compressed during storage, thus avoiding occlusions and facilitating the flushing of air.

However, the implementation of the above-described cartridge into a pump motor frame resulted in a modification of the proposed design. The chord segment of the pump chamber removed from the cartridge was integrated into the pump motor frame, eliminating the need for a separate pump chamber segment. However, insertion of a cartridge lacking a portion of its pump chamber into a pump motor frame sometimes resulted in the pinching of tubing between the pump frame and the cartridge at the frame/cartridge interface, producing the occlusions sought to be avoided by the solution described in the above-noted patent.

SUMMARY OF THE INVENTION

The present invention contemplates improvements to the disposable cartridge used in the pump motor frame of a small peristaltic pump used in medical applications, wherein the cartridge inserted into the pump motor frame incorporates a safety shield which prevents occlusion of the tubing associated with the cartridge at the frame/cartridge interface.

Additional features of the present invention include a ribbed cartridge wall which engages the rotor and minimizes friction of the rotor against the cartridge wall. Further, the improved cartridge of the present invention includes an improved locating feature associated with the frame/cartridge interface, wherein dowel pins provided on the pump motor frame engage dowel pin openings on the cartridge wherein the dowel pin openings have open bottoms to receive dowel pins of various lengths including dowel pins of greater length than would have been accepted by the previous cartridge.

Further, the flexible sidewalls of the cartridge enable a consistent and repeatable fit for the dowel pins of the pump motor frame in the dowel pin openings of the cartridge to assure that the cartridge is rigidly fixed in the pump motor frame.

These and other advantages will be better understood when the detailed description set forth below is considered in conjunction with the drawings provided as described below.

DETAILED DESCRIPTION OF THE PREFERRED EMBODIMENT

Figure 1:
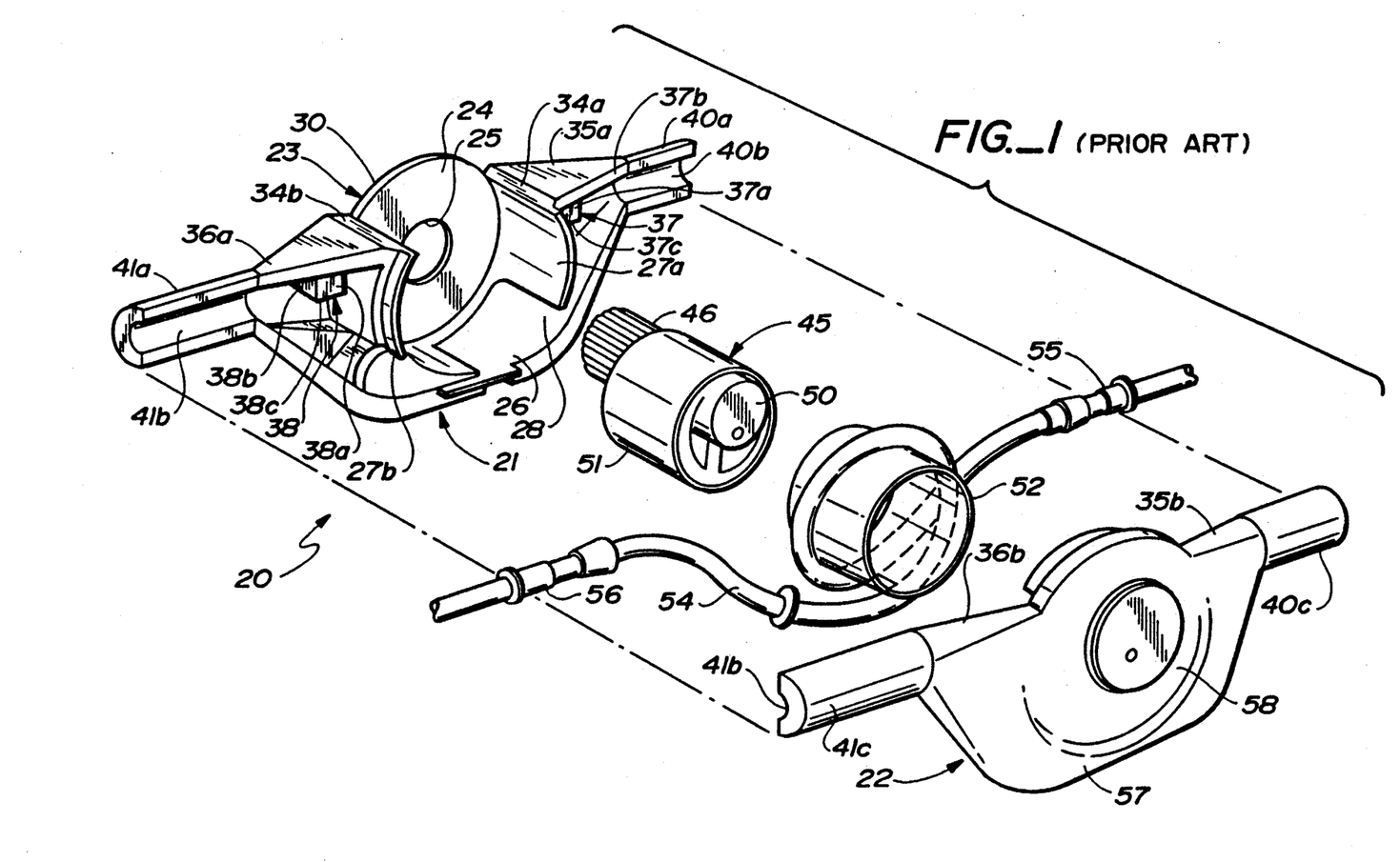
FIG. 1 is an upper right hand exploded perspective view of a prior art cartridge usable in a pump motor frame.
Figure 2:
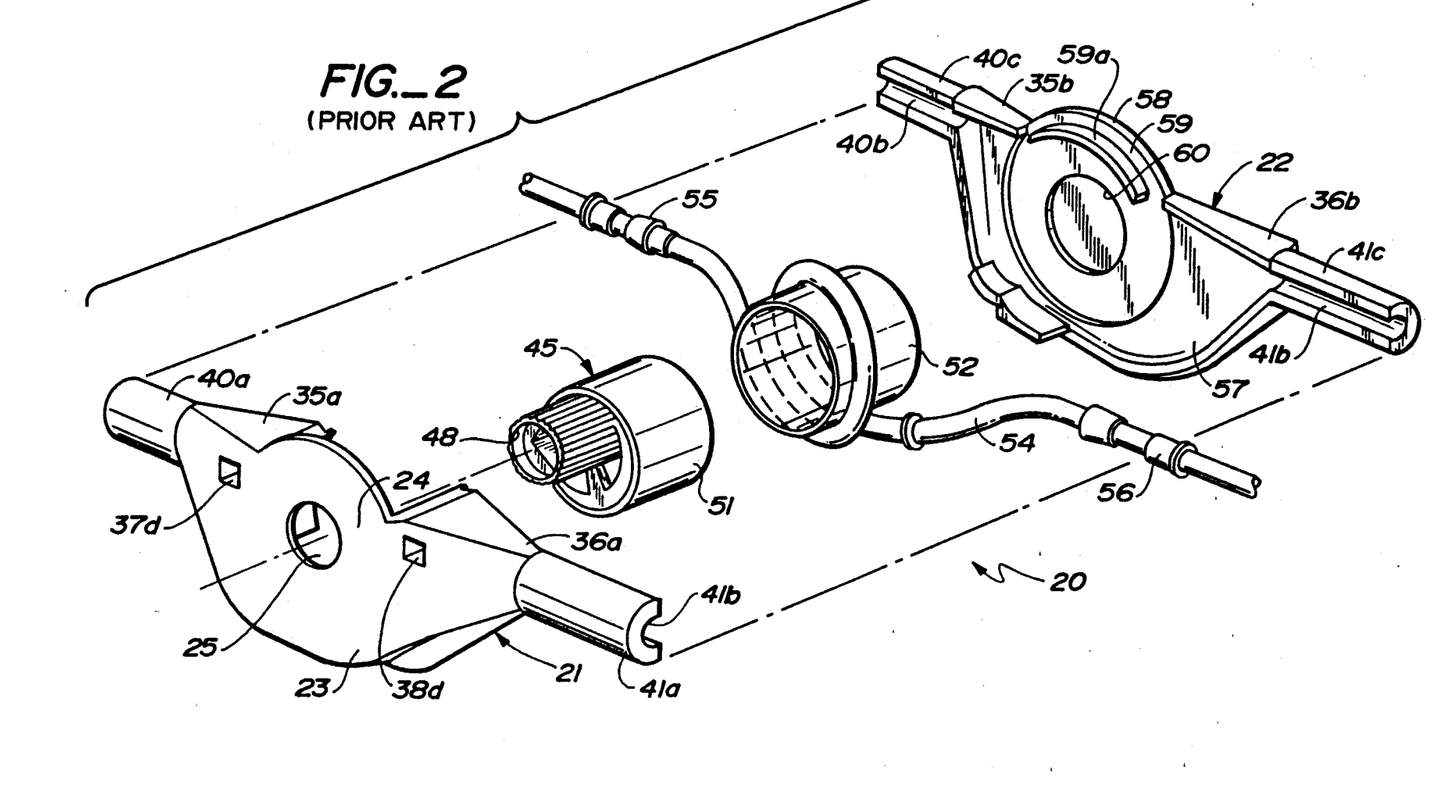
FIG. 2 is an upper left hand exploded perspective view of the cartridge of FIG. 1.

The improved cartridge of the present invention is better understood by first considering prior art cartridge 20 of FIGS. 1 and 2. A prior art cartridge 20 of the prior art comprises a housing 21 and a cover 22. The housing 21 is essentially a one piece molded body including a rear wall 23 having a central circular portion 24 having a central opening 25 therein and concentric therewith. A bottom wall 26, and opposite curved side walls 27a and 27b combine to define a central chamber 28 therein.

Integral with the side walls 27a and 27b are respective top walls 35a and 36a. An open segment 30 is provided between top walls 35a and 36a, the open chord segment 30 comprising an open section of approximately 120° adjacent the circular portion 24 of rear wall 23. Note that side wall 27a is joined to top wall 35a at junction 34a with side wall 27b joined to top wall 36a at junction 34b.

Disposed below the junction of side wall 27a and top wall 28a is a dowel pin receiving member 37, having a bottom wall 37a and side walls 37b and 37c. As better seen in FIG. 2, dowel pin opening 37d of dowel pin receiving member 37 opens into the rear wall 23 of the cartridge housing 21.

A complementary dowel pin receiving member 38 is shown on the opposite side of central opening 25 of rear wall 23. The dowel pin receiving member 38 includes a bottom wall 38a, side walls 38b and 38c, as well as an opening 38d in the rear wall 23 of the cartridge 21.

Extending from opposite ends of main body portion 23 of the cartridge 21 are grooved fitments 40a and 41a each having a respective semicircular channel portion 40b, 41b therein extending into the cartridge chamber 28.

Rotor 45 includes rotor shaft 46 which as received in the opening 25 in rear wall 23. The rotor 45 carries an eccentric cam 51 overlying the rotor shaft 46. The rotor shaft 46 has an open end 48 therein at the end received in the opening 25 and a closed end 50 opposite the open end. A sleeve 52 overlies the rotor 45. Wrapped around the sleeve 52 is a section of flexible tubing 54 having opposite ends, with fittings 55, 56 mounted at opposite ends of the tubing 54, to define an inlet port 55 and an outlet port 56.

The cover 22 comprises a front wall 57 having a central circular portion 58 complementary to the circular central portion 24 of the wall 23 of the housing 21. Within central circular portion 58 is provided a central step down circular portion 60 complementary to the circular portion 58 and concentric therewith. Extending outwardly from central body portion 58 are opposite top wall portions 35b and 36b complementary to top walls 35a and 36a of the housing 21, and disposed at opposite ends are fitments 40c and 41c complementary to fitments 40a and 41a respectively and retaining therein portions of the channel 40b and 41b. An open segment 59 between top wall portions 35b and 36b is complementary to the open segment 30 of the housing 20. A lip 59a extends rearwardly from the front wall 57 at the open segment 59. The lip 59a conforms generally to the arc of central portion 58 at open chord segment 59.

Figure 3:
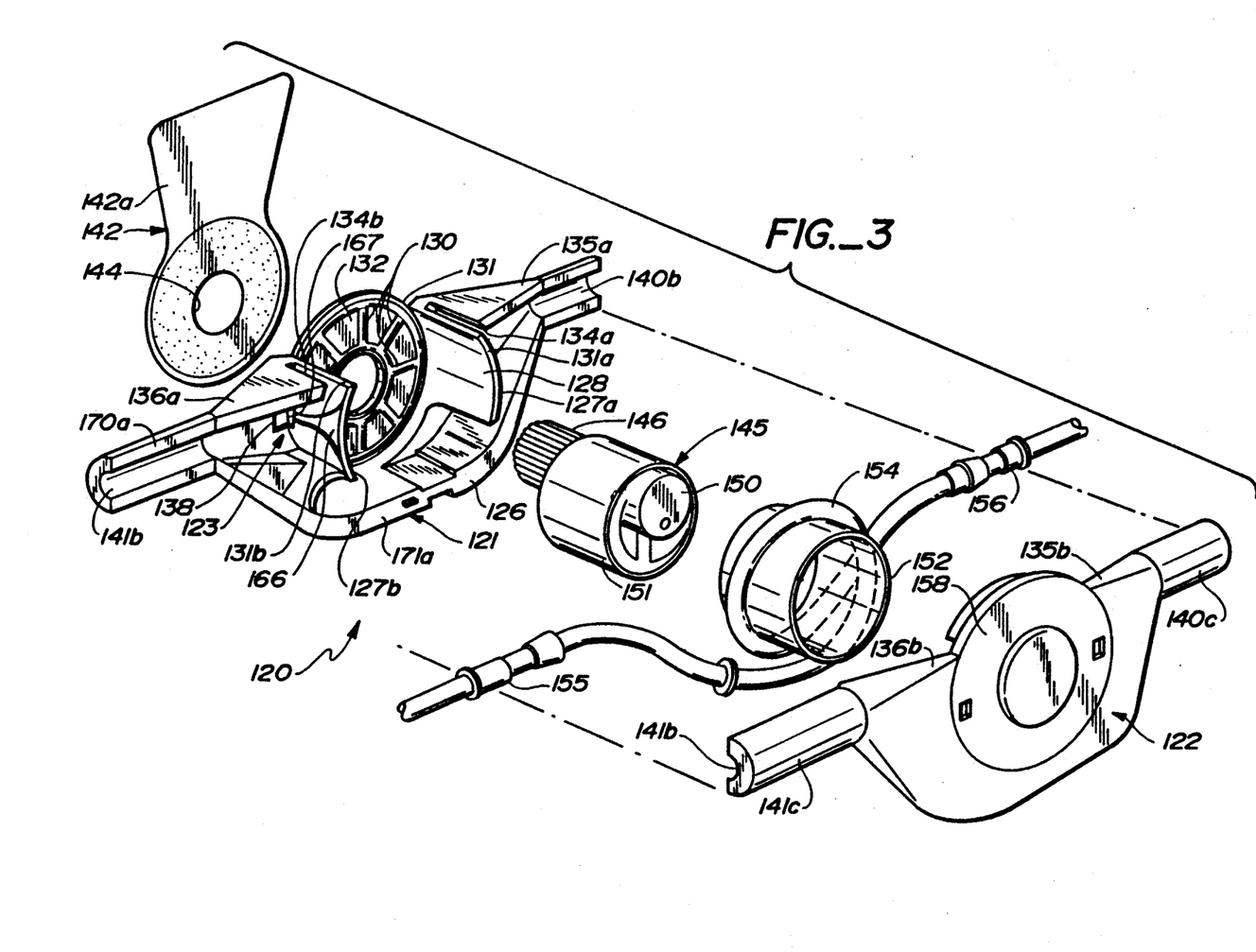
FIG. 3 is an upper right hand exploded perspective view similar to the view of FIG. 1 wherein the improved cartridge of the present invention is shown.
Figure 4:
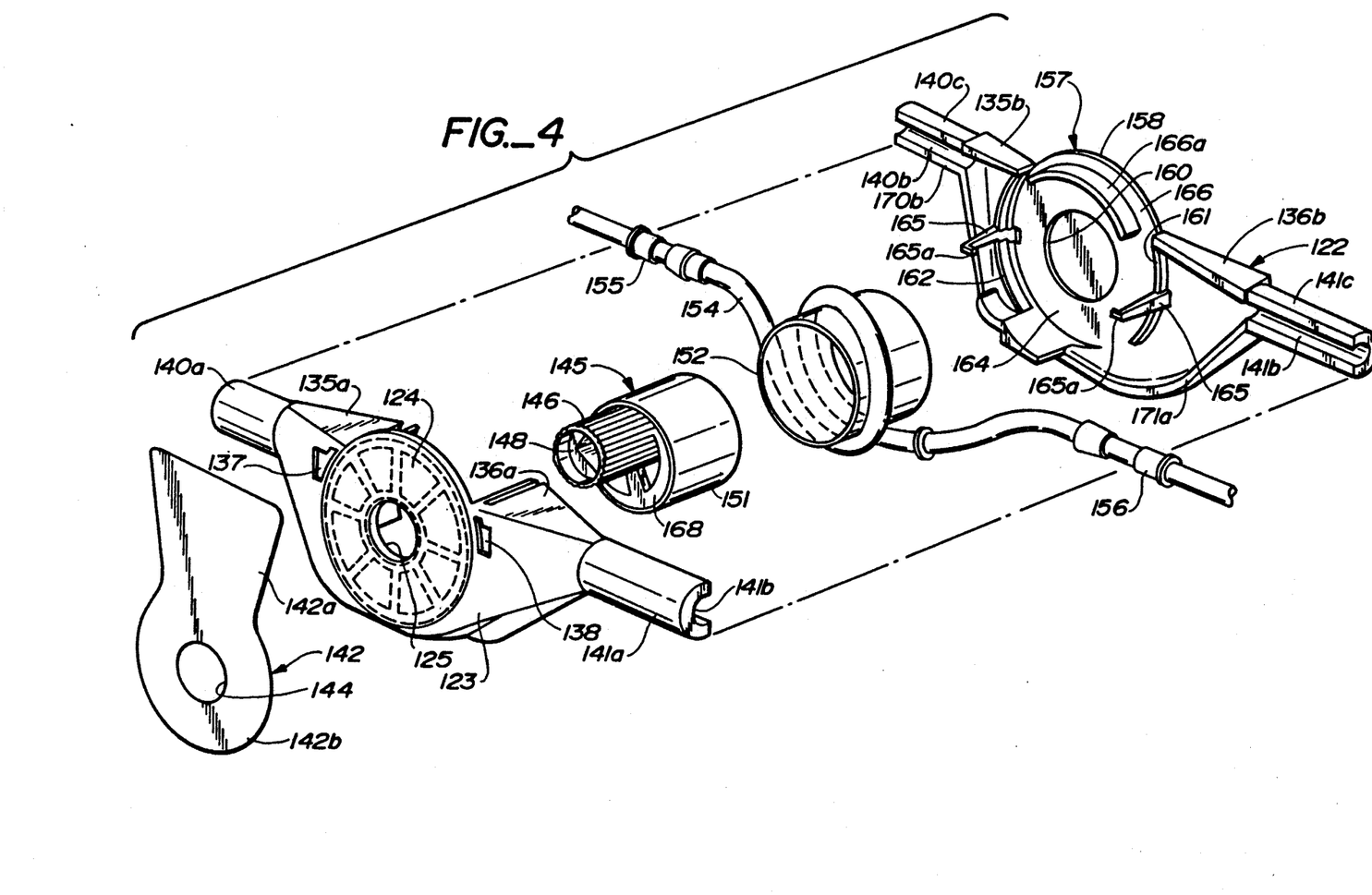
FIG. 4 is an upper left hand exploded perspective view of the cartridge shown in FIG. 3.

FIGS. 3 and 4 define the improved disposable cartridge 120 of the present invention, the improved cartridge having a housing 121 and a cover 122. The housing 121 comprises a rear wall 123 having a circular central portion 124 having a central opening 125 therein and concentric therewith. Curved side walls 127a and 127b combine with bottom wall 126 to define a central chamber 128 therein.

Unlike rear wall 24 of the prior art cartridge 20, central portion 124 of the rear wall 123 includes radially extending ribs 130 which radiate from the central opening 125 to peripheral ribbed edge 131 of the central portion 124 of the rear wall 123. Side walls 127a and 127b include upper edges 131a and 131b which terminate at an outer surface of rear wall 123 to define an open chord segment 132 between upper edges 131a and 131b, the open chord segment 132 being approximately 120° and overlying the chamber 128.

Slot 134a separates side wall 127a from top wall 135a. Slot 134b separates side wall 127b from top wall 136a. Free standing side walls 127a and 128b give the improved cartridge 120 substantially improved flexibility and fit when compared to the prior art cartridge 20. Dowel pin openings 137 and 138 are provided in the rear wall 123 of the housing 121 on opposite sides of central opening 125. Fitments 140a and 141a are provided on opposite ends of rear wall 123 to define respective halves of channels 140b and 141b therein.

Safety shield 142 is a flexible member having an upright flap 142a extending above the top of the cartridge 120. A lower portion 142b of the safety shield 142 generally overlies rear wall 123 with an opening 144 aligned with opening 125 in the rear wall 123.

Rotor 145 comprises a rotor shaft 146 having an open end 148 and a closed end 150. Eccentric cam 151 is rigidly mounted on the rotor shaft 146 near the closed end 150 thereof. A sleeve 152 overlies the cam 151 of the rotor 145. A length of flexible tubing 154 loops around the sleeve 152 and, at respective opposite ends thereof, fittings 155 and 156 define a respective inlet port 155 and an outlet port 156 for the cartridge 120.

Cover 122 includes a front wall 157 having a circular central portion 158, and a step-down central portion 160 concentric with the circular portion 158. Registration surfaces 161 and 162 complementary to side walls 127a and 127b of the housing 121 are formed on a rear face 164 of front wall 157 of the cover 122. A pair of elongated snap-in members 165 having upper snap-in latches 165a extend upwardly from the rear face 164 of front wall 157 on opposite sides of central circular portion 158 of the cover 122, the snap-in members 165 to be received in a pair of complementary tracking grooves 166 provided on opposite outer surfaces of side walls 127a and 127b, which provides rotational alignment between the housing 121 and the cover 122.

The cover 122 includes top wall portions 135b and 136b which are disposed on opposite side of central portion 158 and are complementary with top wall portions 135a and 136a of the housing 121. The top wall portions 135b and 136b engage opposite edges of circular central portion 158 to define an open chord segment 169 of approximately 120° therebetween. A lip 166a conforms generally to the arc of central circular portion 158 and extends rearwardly from the wall 157.

At opposite ends of front wall 157 are provided fitments 140c and 141c which include channel portions 140b and 141b and are complementary to fitments 140a and 141a of the housing 121. The assembly of the disposable cartridge 120 is described below and shown in FIGS. 5-7.

Figure 5:
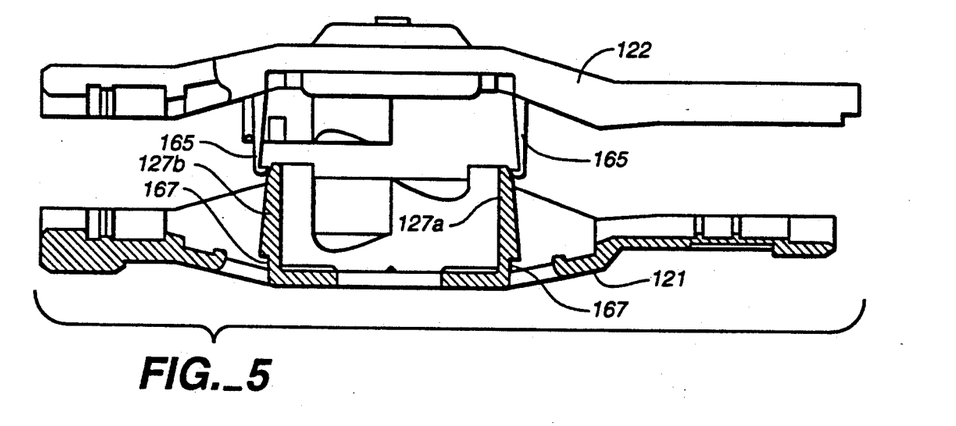
FIG. 5 is a side elevational view, partially in section, of the unassembled housing and cover of the cartridge of the present invention, the housing and cover aligned for snap-fit assembly.
Figure 6:
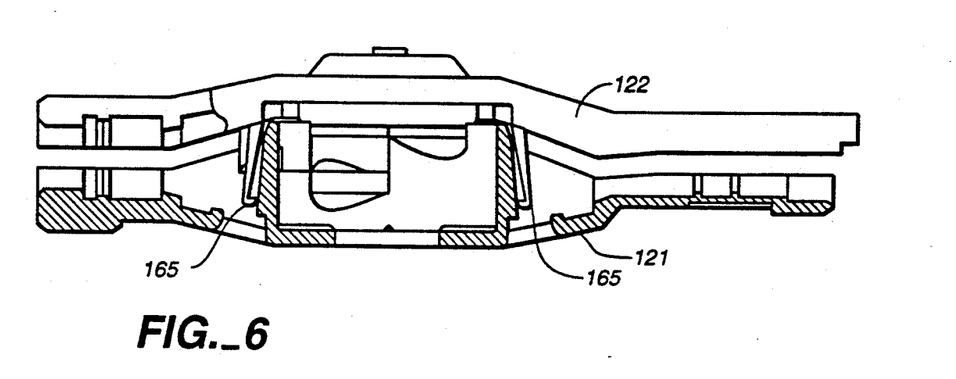
FIG. 6 is a view similar to FIG. 5 in which the assembly of the cover on the housing of the cartridge is in progress.
Figure 7:
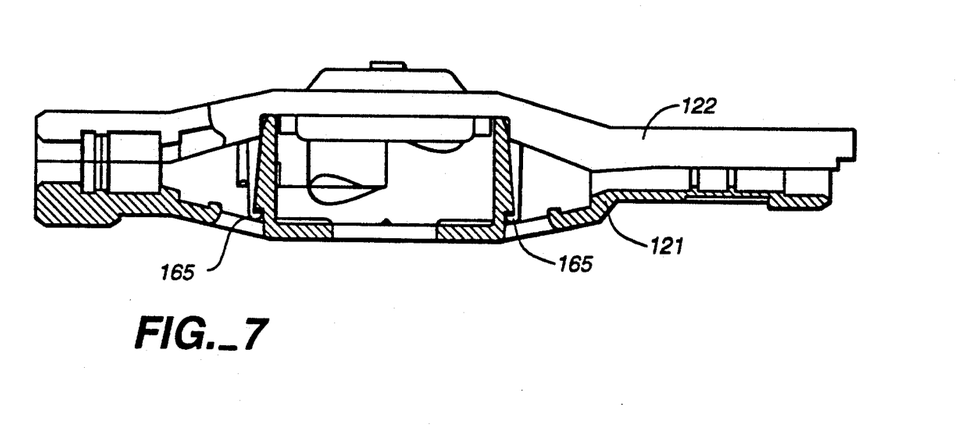
FIG. 7 is a view similar to FIG. 5 in which the housing and the cover of the cartridge of the present invention are in snap-fit engagement.
Figures 8, 9:
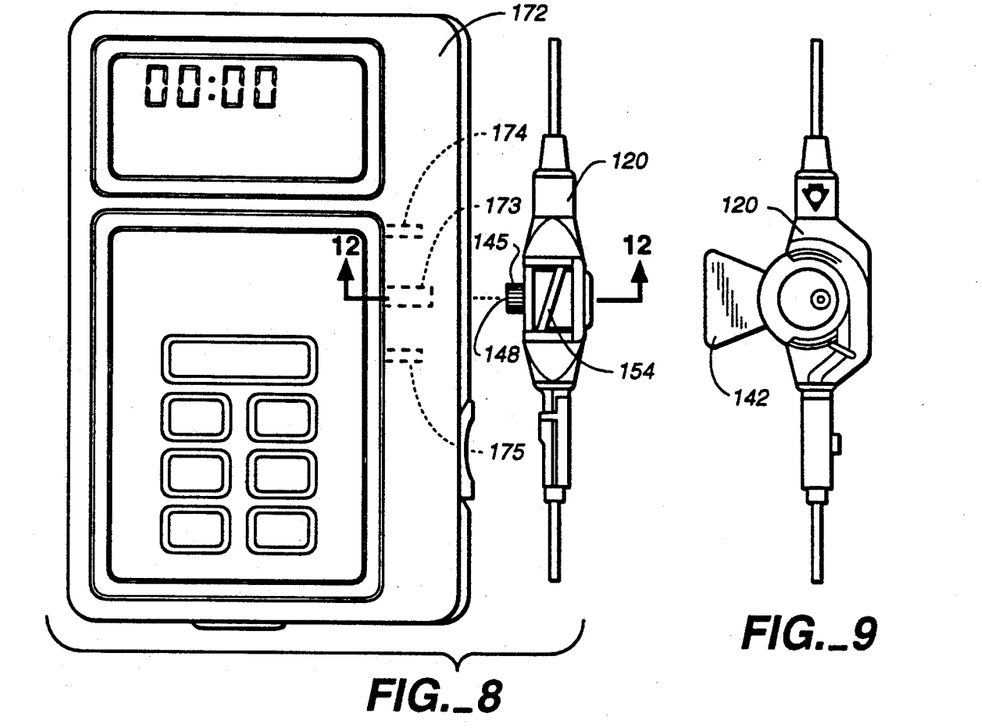
FIG. 8 is a top elevational view of a pump motor frame and cartridge in combination, with the cartridge displaced from the pump motor frame.
FIG. 9 is a side elevation of the cartridge of FIG. 8.
Figure 10:
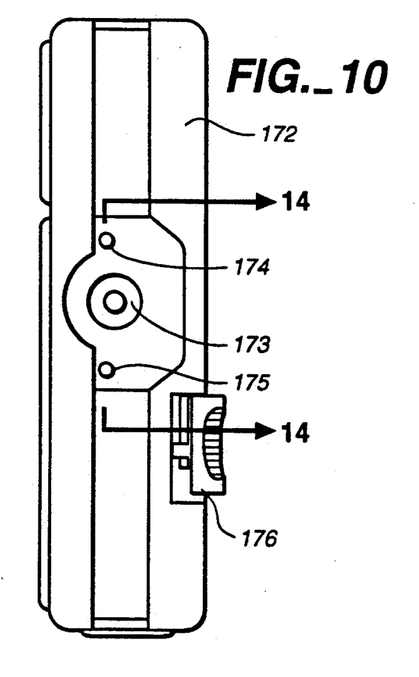
FIG. 10 is a side elevation of the pump motor frame of FIG. 8.
Figure 11:
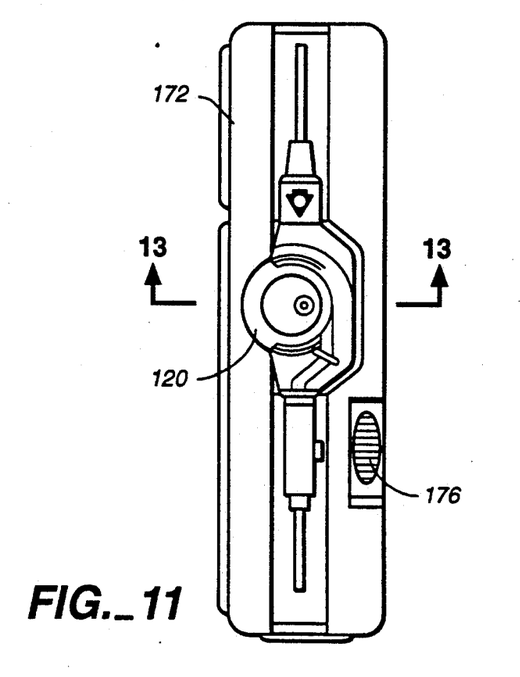
FIG. 11 is a side elevation similar to FIG. 10 in which the cartridge of the present invention as installed in the pump motor frame.

Housing 121 receives the rotor shaft 146 of the rotor 145 in the opening 125 with rear wall 168 of the cam 151 engaging ribs 130 of the central circular rear wall portion 124. Safety shield 142 is received on the motor shaft 146 at opening 144 to overlie the rear wall 123 at central circular portion 125 to be bonded in place thereon.

Sleeve 152 and associated tubing 154 overlie the cam 151 of the rotor 145 with fittings 155 and 156 received in channels 140b and 141b respectively formed by fitments 140a,c and 141a,c respectively.

With the rotor 145 and the sleeve 152 and its associated tubing 154 mounted in place within the housing 121, the cover 122 is mounted on the housing 121 by guiding snap members 165 along the guide tracks 166 on side walls 127a and 127b until each snap member latch 165a engages a respective upper edge 167 of the guide track 166 to snap above that upper edge to hold the cartridge 120 in snap-fit engagement.

In the assembled cartridge 120, the closed end 150 of the rotor 145 is received in the step-down portion 160 of the front wall 157 of the housing 122. Free standing walls 127a and 127b are flexible until captured by mating contoured edges 161, 162 on cover 122. Contoured edges 161, 162 pull flexible side walls 127a, 127b inward to hold the side walls straight, perpendicular to rear wall 123 and front wall 157, and concentric to hole 125. The alignment of the side walls 127a, 127b of the housing 121 with the contoured edges 161, 162 of the cover 122 also holds the hole 125 in the housing aligned with the step-down portion 160 of the cover for optimum rotor performance.

The housing 120 includes an upper parting line 170a and lower parting line 171a that is complementary with an upper parting line 170b and lower parting line 171b on the cover 122. When the housing 120 is joined to the cover 122 in snap-fit engagement, upper parting lines 170a and 170b and lower parting lines 171a and 171b are joined, and housing and cover can be appropriately joined as by ultrasonic welding.

FIGS. 8–11 show a pump motor frame 172 receiving a disposable cartridge 120, the cartridge 120 including a safety shield 142. Motor shaft 173 receives the open end 148 of the rotor 145 with dowel pins 174 and 175 received in dowel pin openings 137 and 138 respectively of the cartridge 120. The pump motor frame 172 includes a latch 176 (FIG. 10) for latching the cartridge 120 in place.

Figure 12:
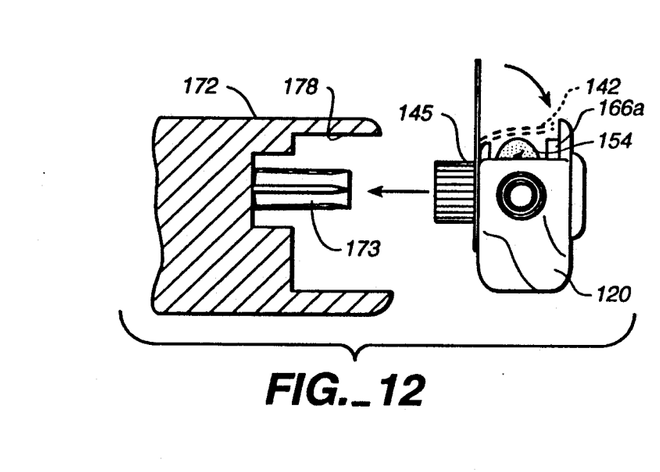
FIG. 12 is a view partially in section, taken along the lines 12—12 of FIG. 8.
Figure 13:
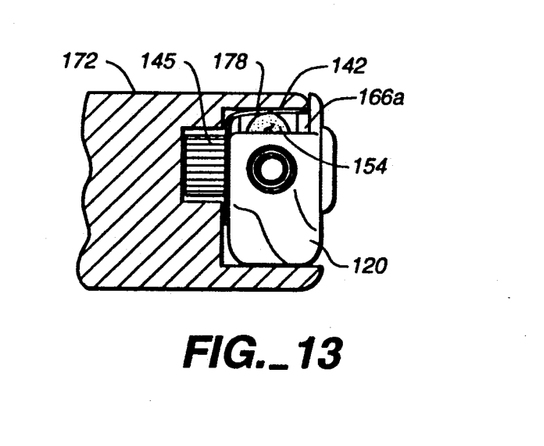
FIG. 13 as a view partially in section, taken along the lines 13—13 of FIG. 11.

As seen in the end views of FIGS. 12 and 13, shown partially in section, motor shaft 173 engages rotor 145 with safety shield 142 engaged by upper edge 178 of pump motor frame 172 to cause the safety shield 142 to overlie the tubing 154 and the lip 166a to prevent pinching or occluding of the tubing 154 as the cartridge 120 is loaded into the pump motor frame 172.

Figure 14:
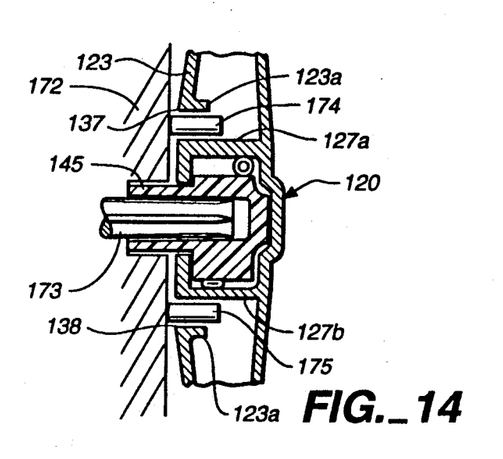
FIG. 14 is a view taken along the lines 14—14 of FIG. 10 with the improved cartridge of the present invention in place.

FIG. 14 shows the relationship of the dowel pins 174 and 175 of the pump motor frame 172 with the cartridge 120. Note the dowel pin openings 137 and 138 of the improved cartridge 120 are, for the most part, merely holes in the rear wall 123 of the cartridge 120. Therefore, greater tolerances are allowed with respect to the spacing of the dowel pins 174 and 175 and greater latitude is allowed with respect to the depth of the dowel pins 174 and 175. Flex walls 123a (FIG. 14) provided in dowel pin openings 137, 138 respectively keep the cartridge 120 aligned concentric over motor shaft 173 to aid in consistent and reliable loading, cartridge to cartridge.

Figure 15:
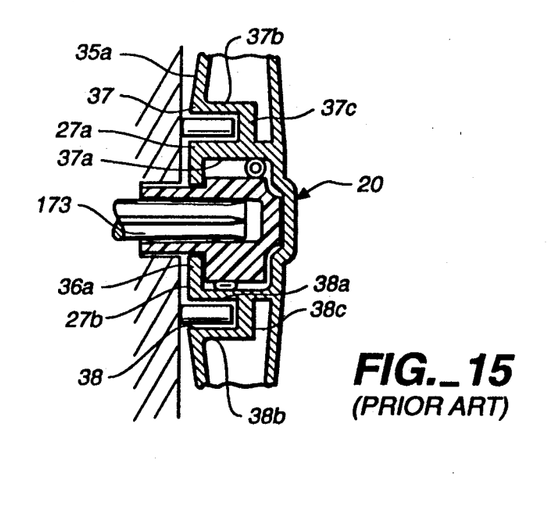
FIG. 15 is a view similar to FIG. 14 with the cartridge of the prior art in place.

Contrast the structure of the cartridge 120 in FIG. 14 with the prior art cartridge 20 in FIG. 15. The cartridge 20 shown in FIG. 15 is an integrally constructed cassette wherein the top wall 35a is connected to side wall 27a whereby side wall 27a is no longer free standing. Moreover, dowel pin member 37 is not merely an open hole in the rear wall 35a but rather a dowel pin holding member 37 having respective side walls 37a and 37b and a bottom wall 37c, therefore severely limiting the positioning of the dowel pin, as well as putting severe restrictions on the length of the dowel pin.

The cartridge 120 may be formed from any suitable material; however, a hard transparent plastic is preferable. It is also preferable to mold the sleeve and rotor from a material having a low coefficient of friction, such as acetal. It is also desirable to lubricate rotor and housing to reduce friction. A fluorosilicone lubricant is preferable to reduce friction at the rotor/cartridge interface.

We claim:

1. In a portable drug infusion pump, an improved segmented peristaltic cartridge comprising a housing, a cover, and an open segment therebetween, said combination defining pump and chamber therein, said cartridge having respective inlet and outlet ports at opposite ends thereof, an eccentric rotor and rotor shaft disposed in said chamber, a sleeve mounted on the rotor, a length of resilient tube looped around said sleeve and having opposite ends engaging respective inlet and outlet ports of the cartridge wherein the improvement comprises:

a housing having a rear segment wherein an arc of approximately 240° forms the internal periphery thereof, a cover segment wherein an arc of approximately 240° forms the internal periphery thereof, a tubing track being created by the space between said housing and said cover wherein said length of resilient tube is spirally wrapped in said track and connected to said inlet and outlet ports, said rear housing segment acting to contain said resilient tube and mating with said cover segment, said inlet and outlet ports being formed by the mating of said housing and cover segments;

a pump frame engaging said housing at the open segment thereof and providing a surface completing a missing chord of said tubing track; and a safety shield disposed on the exterior of said housing segment;

whereby the assembled housing including, with said housing segment, cover segment, eccentric rotor, and tube, the eccentric rotor oriented to press said resilient tubing into the position of said missing chord with the safety shield preventing said resilient tubing from being pinched closed so the tubing may be filled and stored ready for use, requiring the engagement of the motor frame with the cartridge and connection of a rotational drive means to said rotor extremity to deliver liquid medicament to a patient.

2. An improved segmented peristaltic cartridge as claimed in claim 1 wherein the safety shield comprises a flexible member having an opening therein overlying the rotor shaft with an upright member extending above the housing, the member bendable to protect the tubing exposed in the open segment of the cartridge when the cartridge is inserted into the pump motor frame.

3. An improved segmented peristaltic cartridge as claimed in claim 2 wherein the rear segmented housing includes side walls forming the periphery of the internal pump chamber;

the cover segment including registration surfaces complementary to the side walls of the housing, with the side walls of the housing engaging a complementary registration surfaces of the cover when housing and cover are assembled.

4. An improved segmented peristaltic cartridge as claimed in claim 3 wherein the side walls have provided an exterior face thereof tracking grooves, and the cover includes elongated snap-fit members extending upwardly therefrom wherein engagement of the snap-fit members of the cover with the tracking grooves of the housing enables the cover to advance along the housing to an assembled position wherein the snap-fit members engage complementary latching portions of the cover to hold cover and housing in assembled relation.

5. An improved segmented peristaltic cartridge as claimed in claim 4 wherein the cover includes registration openings disposed on opposite sides of a central opening in the cover, such registration openings complementary to locators provided on the pump motor frame to engage the housing with the pump motor frame in assembled relation.

6. An improved segmented peristaltic cartridge as claimed in claim 5 wherein the housing rear wall includes peripheral ribs extending from a central opening therein, said peripheral ribs engaging a rear surface of the rotor to minimize friction between the housing and the rotor.

* * * * *